US010161907B2

(12) United States Patent
Fiala et al.

(10) Patent No.: US 10,161,907 B2
(45) Date of Patent: Dec. 25, 2018

(54) METHOD AND A DETECTION DEVICE FOR EVALUATING THE DISTRIBUTION, DENSITY AND ORIENTATION OF FERROMAGNETIC, ELECTRICALLY CONDUCTIVE FIBRES IN A COMPOSITE MATERIAL

(71) Applicant: VYSOKE UCENI TECHNICKE V BRNE, Brno (CZ)

(72) Inventors: Pavel Fiala, Bilovice nad Svitavou (CZ); Martin J. Friedl, Litomysi-Zahaji (CZ); Leonard Hobst, Brno (CZ); Tereza Komarkova, Brno (CZ)

(73) Assignee: VYSOKE UCENI TECHNICKE V BRNE, Brno (CZ)

( * ) Notice: Subject to any disclaimer, the term of this patent is extended or adjusted under 35 U.S.C. 154(b) by 0 days.

(21) Appl. No.: 15/523,822

(22) PCT Filed: Nov. 3, 2015

(86) PCT No.: PCT/CZ2015/000132
§ 371 (c)(1),
(2) Date: May 2, 2017

(87) PCT Pub. No.: WO2016/070859
PCT Pub. Date: May 12, 2016

(65) Prior Publication Data
US 2017/0343512 A1    Nov. 30, 2017

(30) Foreign Application Priority Data

Nov. 3, 2014  (CZ) .............................. PV 2014-742

(51) Int. Cl.
*G01N 27/82*  (2006.01)
*G01N 33/38*  (2006.01)
(Continued)

(52) U.S. Cl.
CPC ........... *G01N 27/82* (2013.01); *G01N 33/383* (2013.01); *G01N 33/442* (2013.01); *G01N 2033/0003* (2013.01)

(58) Field of Classification Search
CPC . G01N 27/72; G01N 27/745; G01N 33/54326
See application file for complete search history.

(56) References Cited

U.S. PATENT DOCUMENTS

| 4,639,669 A | 1/1987 | Howard et al. |
| 4,755,753 A | 7/1988 | Chern |
| (Continued) | | |

FOREIGN PATENT DOCUMENTS

| EP | 0389916 | 10/1990 |
| EP | 0747733 A2 | 12/1996 |
| (Continued) | | |

OTHER PUBLICATIONS

Faifer, Marco et al., "Nondestructive Testing of Steel-Fiber-Reinforced Concrete Using a Magnetic Approach", IEEE Transactions on Instrumentation and Measurement, May 2011, pp. 1709-1717, vol. 60, issue 5, IEEE (2010).

(Continued)

*Primary Examiner* — Giovanni Astacio-Oquendo
*Assistant Examiner* — Alvaro Fortich
(74) *Attorney, Agent, or Firm* — Avery N. Goldstein; Blue Filament Law PLLC

(57) ABSTRACT

A method and a device for evaluating the distribution and orientation of ferromagnetic, electrically conductive fibers in a composite material are disclosed. The principle consists in repeatable evaluation of the density of ferromagnetic, electrically conductive fibers at the measured location, and such evaluation is performed within a guaranteed scatter range of the measured data and at a guaranteed accuracy rate. A device to perform the method comprises a C, U or (Continued)

E-shaped ferromagnetic core (1) with distributed or uniform winding of the electric coil (2), where the ferromagnetic core (1) exhibits dimensions A, B, and C, for which we have $C \geq 3B$ and $B \approx A$, where A denotes the width of an arm (1.2), B represents the depth of an arm (1.2), and C is the length of the base (1.1). The ferromagnetic core (1) is equipped with at least two electric coils (2) and, to ensure strong electromagnetic coupling on the ferromagnetic core (1), the winding of the electric coil (2) is configured on both arms of the ferromagnetic core (1). The leads of the electric coil (2) winding are, at the winding terminals (3), connected to an external electric circuit (17) including an electric voltage generator (16) with adjustable frequency f and a measuring device (18).

5 Claims, 7 Drawing Sheets

(51) Int. Cl.
*G01N 33/44* (2006.01)
*G01N 33/00* (2006.01)

(56) References Cited

U.S. PATENT DOCUMENTS

| | | | | | |
|---|---|---|---|---|---|
| 5,473,244 | A | * | 12/1995 | Libove | G01R 1/22 324/126 |
| 5,691,645 | A | * | 11/1997 | Acher | G01R 33/1223 29/593 |
| 5,717,332 | A | | 2/1998 | Valborg Hedengren et al. | |
| 6,229,307 | B1 | * | 5/2001 | Umehara | G01R 33/02 324/244 |
| 7,515,387 | B2 | * | 4/2009 | Yuasa | B82Y 10/00 360/324.1 |
| 2003/0067293 | A1 | * | 4/2003 | Golder | G01V 3/107 324/67 |
| 2012/0126803 | A1 | | 5/2012 | Goldfine et al. | |
| 2014/0159707 | A1 | * | 6/2014 | Ashe | H01F 41/02 324/207.16 |

FOREIGN PATENT DOCUMENTS

| | | |
|---|---|---|
| JP | 2002350404 A | 12/2002 |
| WO | 8301505 | 4/1983 |
| WO | 2007136264 | 11/2007 |

OTHER PUBLICATIONS

Ferrara, Liberato, Faifer, Marco, Toscani, Sergio, "A magnetic method for non destructive monitoring of fiber dispersion and orientation in steel fiber reinforced cementitious composites—part 1: method calibration", Materials and Structures (2012), pp. 575-589, vol. 45, RILEM (2011).

Vala, J. and Horak, M., "Nondestructive identification of engineering properties of metal fibre composites", AIP Conference Proceedings (2012), pp. 2208-2212, vol. 1479, issue 1, American Institute of Physics (2012).

Faifer, Marco et al., "Low Frequency Electrical and Magnetic Methods for Non-Destructive Analysis of Fiber Dispersion in Fiber Reinforced Cementitious Composites: An Overview", Sensors (2013), pp. 1300-1318, vol. 13, Copyright by the authors; licensee MDPI, Basel Switzerland (2013).

Ciercoles, Eric Brosa, "Magnetic validation system for steel fiber reinforced concrete", Masters Thesis, Universitat Politecnica de Catalunya, Dec. 19, 2013, pp. 1-81; https://upcommons.upc.edu/bitstream/handle/2099.1/20299/PFC_Magnetic_validation_system_for_steel_fiber_reinforced_concrete_Eric_Brosa.pdf?sequence=4 &isAllowed=y (Retrieved from the Internet on Aug. 24, 2017).

International Search Report dated Mar. 24, 2016 for International Application No. PCT/CZ2015/000132 filed Nov. 3, 2015.

Czech Search Report dated Jul. 17, 2015 for Czech Application No. PV2014-742 filed Nov. 3, 2014.

* cited by examiner

METHOD AND A DETECTION DEVICE FOR EVALUATING THE DISTRIBUTION, DENSITY AND ORIENTATION OF FERROMAGNETIC, ELECTRICALLY CONDUCTIVE FIBRES IN A COMPOSITE MATERIAL

TECHNICAL FIELD

The invention relates to a method and a detection device for evaluating the distribution and orientation of ferromagnetic, electrically conductive fibres in a conductive material, and its applicability lies especially within civil engineering, where it can be utilised to examine floors, carrier beams or other structural components.

STATE OF THE ART

At present, the diagnostics of heterogeneous materials used for structural elements in civil engineering are performed via destructive and non-destructive methods. The former techniques are demonstrably capable of monitoring the condition and distribution of composite components of composite materials, but they exert a destructive effect on materials; the latter methods evaluate the homogeneity of the distribution of composite components of materials, and their disadvantage consists in the merely relative or limited ability to determine accurately the condition, composition and properties of the monitored portion of a structural element.

The related knowledge and characteristics are comprised within several papers, for example "Nondestructive Identification of Engineering Properties of Metal Fibre Composites, J. Vala and M. Horák, or "Nondestructive testing of steel-fibre-reinforced concrete using a magnetic approach" by M. Faifer, R. Ottoboni, S. Toscani and L. Ferrara". The authors of these two research reports examine and propose non-destructive techniques, mainly impedance spectroscopy, for the diagnostics of steel fibre reinforced structural elements. Within the above-named method, the magnetic permeability parameters are evaluated based on defining the anisotropic magnetic environment. In the frequency domain, these parameters are up to 10 kHz, and a ferromagnetic core is used to set the magnetic conditions suitable for evaluation of the impedance of the entire magnetic circuit. From the impedance and its components in the complex component form, we determine, by means of concentrated parameters, the rate of the content of the components, the needle-like shape of the filler and the binder of the composite material (such as steel-fibre-reinforced concrete). The drawback of this technique consists in that it does not define, proportionally or empirically, the density of the metal reinforcement made of fibres uniformly distributed and configured in the composite material. The method does not specify the distribution homogeneity or the position of the fibres; it only defines, via a comparative scale, a higher or a lower rate of density of the ferromagnetic fibres configured in a composite material.

The patent application WO 2007136264 A1 "Non-destructive testing of composite structures" describes a non-destructive testing procedure for fibre-reinforced polymer materials, where an infrared sensor (such as an infrared camera). is used to create images of the tested object. This object is generally a polymer, fibre-reinforced material. According to the invention described in the said patent application, a group of resistance wires is heated during or before the testing of the object, and the heat acts internally, through the set of electrically resistive wires suitably incorporated in the reinforcing fibrous structure of the material. Improved heating of the region is captured by means of an infrared sensor. Thus, in a polymer material, defects of the reinforcing fibres can become easy to recognise during the test. The main application field lies in the production and appropriate verification of the said materials, for example within the manufacturing of aerospace components. The method is based on infrared detection of reflected waves, and therefore it remains outside the scope of the object of invention specified above.

The techniques or devices described and published to date have not solved sufficiently the evaluation of electrically conductive ferromagnetic fibres with respect to other, non-magnetic matter, including the components or parts of a composite (such as steel-fibre-reinforced concrete).

The aim of the invention presented herein is to propose a method and a device for evaluating the distribution and orientation of ferromagnetic, electrically conductive fibres in a composite material. The technique consists in repeatable evaluation of the density of ferromagnetic, electrically conductive fibres at the measured location, and such evaluation is performed within a guaranteed scatter range of the measured data and at a guaranteed accuracy rate.

SUMMARY OF THE INVENTION

The aim of the invention is achieved by designing a method to evaluate the distribution and orientation of ferromagnetic, electrically conductive formations in a composite material, the evaluation procedure being characterised in that, within the initial step, electric coils configured on the arms of a C, U or E-shaped ferromagnetic core are set to a frequency f and excited at $f_{sq3}$ in such a manner that the frequency f corresponds to the resonance with the quality factor $$Q_{sq3} = \frac{1}{\sqrt{3}} Q_{max};$$

subsequently, at a position defined by the distance D from the surface of the monitored composite material sample, the complex impedance $\hat{Z}$ is recorded in both the component and the exponential forms. Then, within the second step, the position of the ferromagnetic core is changed via rotating it by a rotation angle along the axis of one of the arms of the said core, and the complex impedance $\hat{Z}$ in both the component and the exponential forms is measured and recorded. The third step comprises a change and recording of the complex impedance $\hat{Z}$ according to the second step, and at this stage we again apply the said rotation angle to change the position of the ferromagnetic core until the arm is rotated by 360°. Subsequently, within the fourth step, we use the results from the first to the third steps to evaluate—from the formulas for the impedance $\hat{Z}$ and dissipated power P—the mass density of the ferromagnetic or ferromagnetic and electrically conductive formations of the composite material sample; the evaluation is performed at the measured location. In the fifth step, the frequency f of the detection and measuring device is set to $f_{0.5}$ in such a manner that the resonance corresponds to the factor $$Q_{0.5} = \frac{1}{2} Q_{max}$$

for the original point of measurement and distance D, and measurement is performed in accordance with the second and third steps. Then, using the data thus obtained, we evaluate the distribution homogeneity and orientation of the ferromagnetic or ferromagnetic and electrically conductive formations of the composite material sample at the original point of measurement. The sixth step consists in that the electric coil (2) is set to the frequency $f_{0.5}$ and excited such that the frequency f corresponds to the resonance $$Q_{0.5} = \frac{1}{2} Q_{max}$$

and the ferromagnetic core is shifted to the original point of measurement by a distance dX and a distance dY, the said distances dX and dY being oriented with respect to the surface of the monitored composite material sample, and the defined distance D from the surface of the monitored composite material sample is maintained; subsequently, the complex impedance $\hat{Z}$ is recorded in both the component and the exponential forms. Then a shift by the distances –dX, dY with respect to the original point of measurement is performed, and the complex impedance $\hat{Z}$ is recorded in both the component and the exponential forms; after that, there follows a shift by the distances dX, –dY with respect to the original point of measurement, and the complex impedance $\hat{Z}$ is recorded in both the component and the exponential forms; finally, a shift by the distances –dX, –dY with respect to the original point of measurement is performed, and the complex impedance $\hat{Z}$ is recorded in both the component and the exponential forms. Then, using the measurements thus performed, we carry out a more accurate evaluation of the density and volume of the monitored component in the tested composite material sample; the established records of the complex impedance $\hat{Z}$ are subsequently used to calculate the mean value of the density and volume of the monitored component. The seventh step then comprises the setting of a new position of the ferromagnetic core, namely the setting to a new measurement point; such setting ought to be, in the direction of the coordinate x, different by at least a distance greater than the length C of the base 1.1 plus double the width A of an arm 1.2, equalling C+2A; in performing this step, we proceed according to the dimensions of the ferromagnetic core. After setting the new position of the ferromagnetic core, the quantities are measured and evaluated in accordance with the first to the sixth steps, and we thus obtain the numerical and graphical evaluation of the distribution, density and orientation of the monitored component of the tested composite material sample along its entire surface, the said material being ferromagnetic or ferromagnetic and electrically conductive formations.

The technique proposed herein eliminates the above-specified drawbacks, bringing a solution for the methodical evaluation of not only the homogeneity of distribution but also the spatial cluster orientation and mass density in ferromagnetic, electrically conductive and non-conductive fibres in the measured region.

Advantageously, the discussed method enables us both to change the device sensitivity under identical settings of the measurement system and to set the conditions for various composite material types; furthermore, the technique is not limited to steel-fibre-reinforced concrete only but can be used in other applications, such as some carbon composites potentially utilisable in aerospace engineering.

The device to perform the method according to this invention, namely the evaluation of the electromagnetic properties of ferromagnetic, electrically conductive portions of a composite material filler, can be manufactured using the structure of a ferromagnetic core with an electrical winding, such as the C, U or E-shaped one, which is made as a partially distributed or fully uniform winding of an electric coil. The winding is advantageously split between the arms of the ferromagnetic core to ensure strong electromagnetic coupling with the tested electromagnetic material, which comprises a filler and a bond.

The detecting device to perform the method is connected to a magnetic circuit designed such that its resonant frequency in free space lies between 100 kHz and 2 GHz. The choice of the frequency f depends on the parameters of the tested composite material (the density, volume and distribution of the ferromagnetic or ferromagnetic and electrically conductive components) and on the required measurement depth from the surface of the composite material sample. The detecting and measuring device consists of an impedance meter and is connected to an electric coil exciting a magnetic flux c, as shown in FIG. 1a. A ferromagnetic core with the electrical winding of the exciting electric coil is attached to the composite material sample. The impedance meter included in an external electrical circuit evaluates the impedance and its changes in both the component and the exponential forms. The frequency f of the exciting circuit of the detecting and measuring device is set to be located at the heel of the resonance curve, FIG. 2. The connected electric coils are configured on the ferromagnetic core, which is located at a preset distance "D" from the surface of the tested composite material. During the motion of the core at the preset distance "D" from the surface of the composite material, there occur changes in the measured impedance $\hat{Z}$; this impedance is evaluated by the detecting and measuring device, and its change is further recorded via a portion of the external electrical circuit. Using the result of the change, the specific density of the ferromagnetic components and the volume V of the composite material are then interpreted depending on the given position of the ferromagnetic core. The dimension A of the ferromagnetic core can assume dimensions of between 1 mm and 100 mm, and the said core can be manufactured of ferrite, ferrite grains, oriented folded sheet metal, solid ferromagnetic metal (such as pure Fe), nanomaterial grains, Ni, amorphous material, combined materials (such as ferrite) or pure iron with a nanolayer of Ni. The manufacturing is to be invariably performed in such a manner that, for the limit frequency of 2 GHz, any core constructed as defined above exhibits a magnetic relative permeability value higher than 1. Generally, the advantageous version exhibits a value higher than 100.

BRIEF DESCRIPTION OF THE DRAWINGS

The invention is schematically represented in a related drawing, where.

EXEMPLARY EMBODIMENT OF THE INVENTION

Figure 1A:
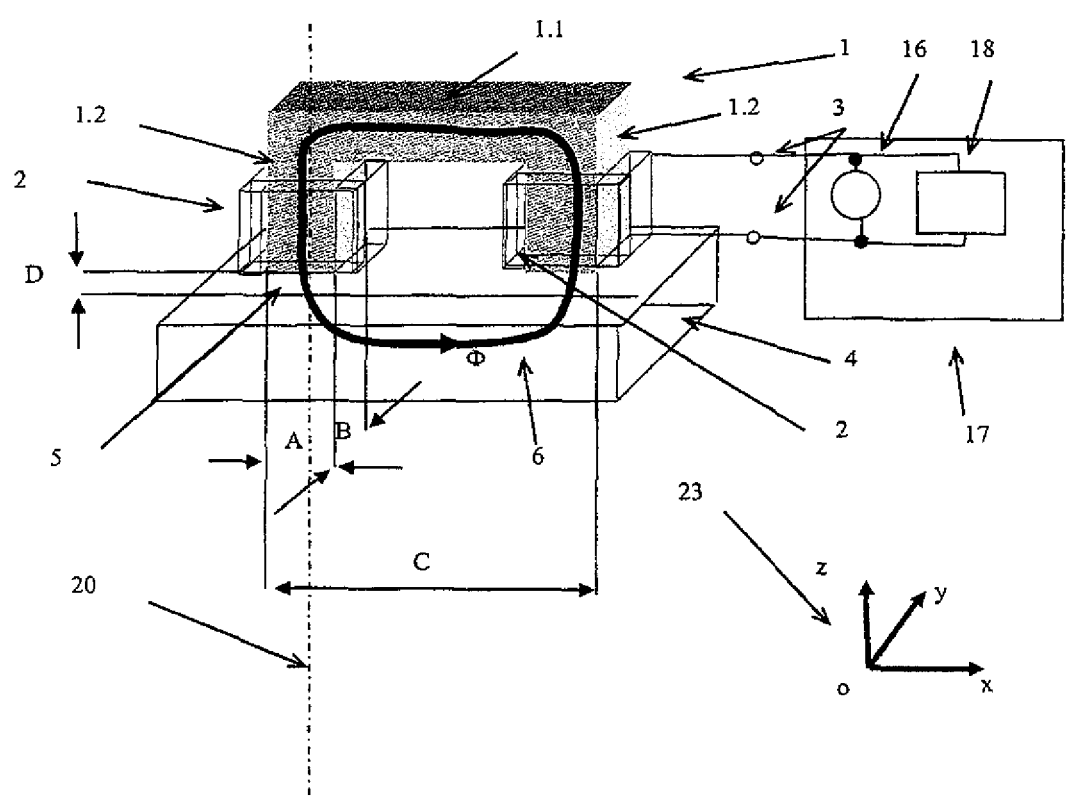
FIG. 1a shows the mutual configuration of the electric coil and the ferromagnetic core with respect to the tested composite material sample.
Figure 2:
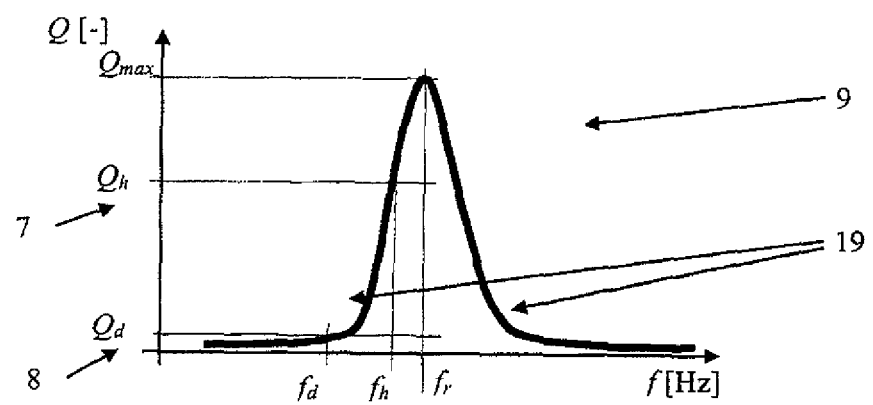
FIG. 2 shows the resonance curve behaviour via the quality factor, specifies the maximum value of the curve $Q_r$ at the frequency $f_r$, and indicates the quantities $Q_d$, $f_d$ at the heel of the resonance curve and $Q_h$, $f_h$ in the interval between the heel and the peak of the said curve.
Figure 3:
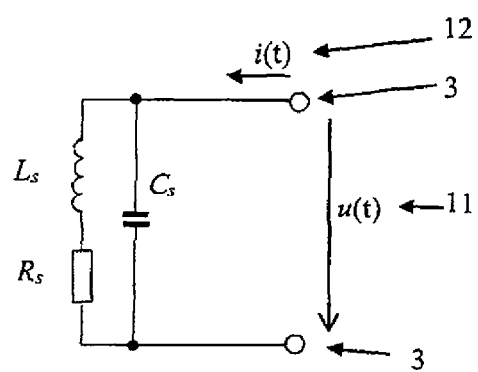
FIG. 3 presents a schematic diagram of an equivalent electrical model of the electric coil wound on the ferromagnetic core, and the said schematic diagram is expressed by means of concentrated parameters, and we have the frequency f of the quantities of electric current and voltage in the near-resonant mode, for which there holds the interval $0.1f_r \geq f \geq 10f_r$.
Figure 4:
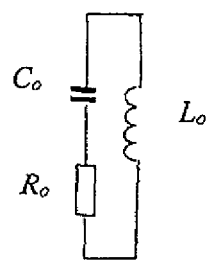
FIG. 4 displays, by means of an electrical diagram and concentrated parameters, a model of the examined composite material sample within the described method of non-destructive evaluation of material properties according to the present invention.

The present invention relates to and proposes a method and a detection device for evaluating the electromagnetic properties of ferromagnetic, electrically conductive parts of a composite material, the purpose of the said device being to perform the method. The detection device comprises a ferromagnetic core 1 consisting of a base 1.1, which connects two arms 1.2 having an electrical winding; the ferromagnetic core 1 is C, U or E-shaped, and the winding of the electric coil is distributed or uniform, as shown in FIG. 1a. The ferromagnetic core 1 having the dimensions A, B, C and the axis 20 is advantageously made of a ferrite material; for the said dimensions, we have C≥3B and B≅A, where A denotes the width of an arm 1.2, B represents the depth of an arm 1.2, and C is the length of the base 1.1. The ferromagnetic core 1 is equipped with two electric coils 2 wound on the arms 1.2 and connected in series, the coil leads being terminated at terminals 3 of the winding. To ensure strong magnetic coupling between the ferromagnetic core 1 and the examined volume V of the composite material sample 4 at the original point of measurement 21, the winding of the electric coil 2 is advantageously configured on both arms 1.2 of the ferromagnetic core 1, and the leads of the winding of the electric coil 2 are, at the terminals 3 of the winding, connected to an external electrical circuit 17, which comprises an electric voltage generator 16 with adjustable frequency f and a detection and measuring device 18, the said device advantageously being an impedance meter. The ends of the arms 1.2 of the ferromagnetic core 1 are placed at a distance D from the surface of the examined composite material sample 4. Thus, a magnetic flux Φ is formed which advantageously closes via a magnetic circuit 6 comprising the ferromagnetic core 1 and the examined volume V of the composite material sample 4. The winding of the electric coil 2 is designed in such a manner that the frequency of the electric voltage generator 16 creates resonance, within the interval of between 200 MHz and 2 GHz, as is shown in FIG. 2; the choice of the frequency f depends on the parameters of the examined volume V of the composite material sample 4 and on the required testing depth from the surface of the examined volume V of the composite material sample 4. The external electrical circuit 17 contains a detection and measuring device 18, which evaluates the complex impedance $\hat{Z}$ of the connected electric coil 2, as shown in FIG. 1a. The detection and measuring device 18 then evaluates the complex impedance $\hat{Z}$ and its changes in both the component and the exponential forms. The frequency f of the electric voltage generator 16 included in the external electrical circuit 17 is set to be located at the foot of the resonance curve 19, FIG. 2, and the said frequency is further defined by the lower frequency $f_d$ with the lower limit 8 of the quality factor $Q_d$ and the upper frequency $f_h$ with the upper limit 7 of the quality factor $Q_h$. The resonance effect will occur if the parameters are set according to the equivalent model scheme, FIG. 5, where the concentrated parameters are described by the inductions L, capacities C, resistors R and mutual induction M. With the parameters set in this manner, the resonant frequency f of the electric voltage generator 16 and the external electrical circuit 17 is within the interval of between 100 kHz and 2 GHz and, simultaneously, within the interval defined by the lower frequency $f_d$ with the lower limit 8 of the quality factor $Q_d$ and the upper frequency $f_h$ with the upper limit 7 of the quality factor $Q_h$. Further, the property of the homogeneity of the examined volume V in the composite material sample 4 can be described via the scheme of the equivalent model with concentrated parameters, which include the capacity $C_0$, resistor $R_0$ and inductance $L_0$, as indicated in FIG. 4. The parameters of this model are given by the quality of the examined volume V of the composite material sample 4; the properties of the ferromagnetic core 1 and the air gap 5 can be described via the scheme of the equivalent model with concentrated parameters, which include the capacity $C_s$, resistor $R_s$ and inductance $L_s$, as shown in FIG. 3. The property of the magnetic circuit 6, which carries the magnetic flux Φ, and comprises the ferromagnetic core 1, the winding of the electric coil 2 and the air gap 5, is given by the distance D between the ends of the arms 1.2 of the ferromagnetic core 1 and the surface of the examined composite material sample 4. The parts of the investigated volume V where the monitored formations of the composite material sample 4 are present can be characterised via the equivalent model with concentrated parameters according to FIG. 5, and these parts are bound by an electromagnetic coupling 10 to the ferromagnetic core 1. The said parts of the investigated volume V where the monitored formations are present can be described by means of the capacity $C_s$, resistor $R_s$, inductance $L_s$ and electromagnetic properties characterising the ferromagnetic core 1, the winding of the electromagnetic coil 2, the air gap 5 (which occupies the space between the end of the ferromagnetic core 1 and the surface of the examined composite material sample 4, inductance $L_0$, capacity $C_0$, resistor $R_0$ (FIG. 4) and mutual inductance M (FIG. 5); the said elements then characterise the parameters materialised by the winding of the electric coil 2 on the ferromagnetic core 1 supplied via leads on the terminals 3 of the electric coil 2 winding. The feeding is further facilitated via the external electrical circuit 17 comprising an electric voltage generator 16 with settable frequency f, the said circuit creating on the terminals 3 of the winding of the electric coil 2 instantaneous values 12 of the electric voltage u (t), and instantaneous values 12 of the electric current i(t) pass through the terminals 3 of the winding of the electric coil 2. Then, the detection and measuring device 18 evaluates the complex impedance $\hat{Z}$ and its changes as specified within the present invention.

The frequency f of the exciting signal of the detection and measuring device 18 is set in such a manner that the resonance quality factor $Q_h$ could assume the values of $$Q_{0.5} = \frac{1}{2} Q_{max}, \ Q_{sq2} = \frac{1}{\sqrt{2}} Q_{max} \ \text{or} \ Q_{sq3} = \frac{1}{\sqrt{3}} Q_{max};$$

the said factor will not assume values below the magnitude of the factor $Q_d$ (FIG. 2). In the experimental setting, the values proved to be beneficial for the final evaluation of the location with inhomogeneous distribution of the composite material components. The complex impedance $\hat{Z}$ of the harmonic behaviour of components of the electric and magnetic field can be written as $$\hat{Z} = \frac{|\hat{E}|}{|\hat{H}|}, \tag{1}$$

where $\hat{E}$ is the complex vector of the electric field intensity, and $\hat{H}$ is the complex vector of the magnetic field intensity. The complex vector of the electric power specific density can be written in the form $$\hat{\Pi} = \hat{E} \times \hat{H}, \tag{2}$$

where the symbol × denotes the vector product. Then—for the connected circuit according to FIG. 1a—the complex impedance $\hat{Z}$ in the exponential form, containing components of the electric and magnetic field of the given configuration of the magnetic circuit 6 and the composite material sample 4, is written as $$\hat{Z}_0 = \frac{\|\hat{E}\|}{\|\hat{H}\|} \angle \varphi_0, \tag{3}$$

where $\angle \varphi_0$ expresses the complex number angle in the exponential form, $\|\hat{E}\|$ is the vector module of the electric field intensity, $\|\hat{H}\|$ denotes the vector module of the magnetic field intensity, and the complex impedance $\hat{Z}$, consisting of components obtained from the detection and measuring device 18, is written as $$\hat{Z}_0 = \frac{|\hat{u}|}{|\hat{i}|} \angle \varphi_0, \tag{4}$$

where $|\hat{u}|$ is the module of the instantaneous value of electric voltage, $|\hat{i}|$ denotes the module of the instantaneous value of electric current, and $\hat{U}$ represents the complex form of the electric voltage on the terminals 3 of the electric coil 2, with equivalent expression via concentrated parameters (FIG. 3); the said coil is configured on the ferromagnetic core 1, as indicated in FIG. 1a. $\hat{I}$ then is the complex form of the electric current flowing through the electric coil 2, with equivalent expression via concentrated parameters (see the equivalent diagram in FIG. 3), on the ferromagnetic core 1, as shown in FIG. 1a. For the preset resonant frequency $f_r$ of the entire setup, which consists of the detection and measuring device 18 and the electric coil 2 wound on the arms 1.2 of the ferromagnetic core 1 at the defined distance D from the composite material sample 4, we have—for the complex impedance $\hat{Z}$ in the exponential form—the formula $$\hat{Z}_0 |_{f_r} = \frac{\|\hat{E}\|}{\|\hat{H}\|} \angle \varphi_0, \ \varphi_0 \cong 0. \tag{5}$$

For the component form, the complex impedance is written as $$\hat{Z}_0 |_{f_r} = Z_{0,Re} + jZ_{0,Im}, \ \forall \ f = f_r \ \text{we have} \ Z_{0,Im} \cong 0,$$

where $Z_{0,Re}, Z_{0,Im}$ are the real and imaginary components of the complex impedance $\hat{Z}$, and we also have the proportion $$Z_{0,Re} \square \frac{P}{I^2},$$

where P is the dissipated electric power in the region with volume V, in the measured part of the composite material, and I is the module of electric currents closing in the measured region of the composite material sample 4.

Figure 5:
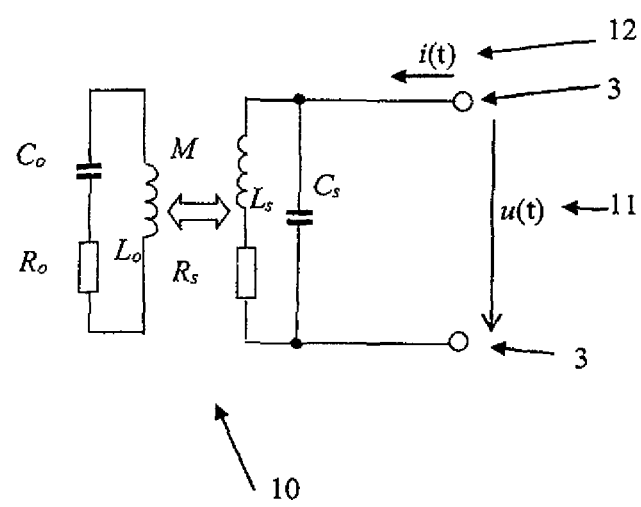
FIG. 5 shows, via an electrical diagram, a model with concentrated parameters representing the situation in the area close to the resonance of the entire configuration of both an electric coil wound on a ferromagnetic core and an electromagnetic field bound by the region of a part of the composite material sample.

If the entire resonant system is not set within the area of resonance, as indicated in FIGS. 2 and 5, the complex resonance $\hat{Z}$ changes, and we have $$\hat{Z}_0 |_{f \neq f_r} = \frac{\|\hat{E}\|}{\|\hat{H}\|} \angle \varphi_0, \ \varphi_0 \neq 0. \tag{6}$$

The change of resonance also for the preset frequency $f_r$ of the detection and measuring device 18 and for the connected electric coil 2 wound on the arms 1.2 of the ferromagnetic core 1 occurs in such a manner that—with respect to the preset reference state with a defined volume V and the distribution of components of the monitored composite material sample 4, and given identical distances D between the ferromagnetic core 1 and the surface of the composite material sample 4—the volume or sense of distribution or the volume and sense of distribution of a part of the composite material sample 4 changed in the monitored area of the sample. The material consists in ferromagnetic formations, such as ones having an acicular shape, used as the filler in the steel-fibre-reinforced concrete. The dissipated electric power P is bound to the area density of the active power from expression (2), according to the following formula:

$$P = \int_{S_{jha}} \|\hat{\Pi}\| \square dS, \tag{7}$$

where dS is the vector of the element of the surface area of the measured part of the composite material sample 4.

Using the relationships expressed in formulas (1) to (7), it is possible, as set forth in this invention, to calibrate and evaluate individual parameters of the desired properties of the composite material samples 4, for example the density, orientation and uniformity of distribution of the filler formations.

The frequency f of the detection and measuring device 18 is set such that the resonance $$Q_{0.5} = \frac{1}{2} Q_{max}$$

occurs, as shown in FIG. 2, which enables very sensitive setting of the detection technique; this procedure is suitable for evaluating the distribution of formations of the composite material with respect to its homogeneity.

The frequency f of the detection and measuring device 18 is set such that the resonance $$Q_{sq2} = \frac{1}{\sqrt{2}} Q_{max}$$

occurs, which leads to less sensitive sensing of the inhomogeneity of distribution of formations of the composite material but is also suitable for evaluating the density of the monitored formations in the composite material sample 4, the said formations being ferromagnetic or ferromagnetic and electrically conductive.

Alternatively, the frequency f of the detection and measuring device 18 is set such that the resonance $$Q_{sq3} = \frac{1}{\sqrt{3}} Q_{max}$$

occurs, which is suitable for accurate evaluation of the density of the monitored component in the composite material sample 4, the said material being ferromagnetic or ferromagnetic and electrically conductive formations. The original point of measurement 21 denotes the space defined by the position of the axis 20 and by the space achievable by rotating an arm 1.2 along the axis 20 at the angle of 0-360°. When the position of the axis 20 is changed by the distances dX and dY, we set a new point of measurement 22 and define a new space.

The procedure for evaluating the distribution and orientation of ferromagnetic, electrically conductive fibres in the composite material is as follows:

In the first step, the electric coil 2 wound on the arms 1.2 of the ferromagnetic core 1 and connected to the detection and measuring device 18 is set to a frequency f and excited in such a manner that the frequency corresponds to the resonance $$Q_{sq3} = \frac{1}{\sqrt{3}} Q_{max}.$$

In this position having the defined distance D from the surface of the monitored composite material sample 4, the complex impedance $\hat{Z}$ is recorded in both the component and the exponential forms.

Then, within the second step, the position of the ferromagnetic core 1 is changed via rotating it by an angle of rotation 24 (such as 10°) along the axis 20 of one of the arms 1.2 of the said core 1, and the complex impedance $\hat{Z}$ in both the component and the exponential forms is measured and recorded.

The third step comprises a change and recording of the complex impedance $\hat{Z}$ according to the second step, and these operations are performed such that the change of the position of the ferromagnetic core 1 by the angle of rotation 24 is progressively repeated until the arm has rotated by 360°.

Subsequently, within the fourth step, we use the results from the first to the third steps to evaluate, from the formulas for the impedance $\hat{Z}$ and the dissipated power P, the mass density of the ferromagnetic or ferromagnetic and electrically conductive formations of the composite material sample 4 at the measured location of the original point of measurement 21.

In the fifth step, the frequency f in the detection and measuring device 18 is set to $f_{0.5}$ in such a manner that the resonance $$Q_{0.5} = \frac{1}{2} Q_{max}$$

occurs for the same measured location of the original point of measurement 21 and the air gap 5 at the distance D, and measurement is performed in accordance with the second and third steps. Then, using the data thus obtained, we evaluate the homogeneity of distribution of the composite material components at the monitored location, namely the original point of measurement 21, and we also evaluate the orientation of the monitored composite material component, the said material being ferromagnetic or ferromagnetic and electrically conductive formations. The acquired results of the complex impedance $\hat{Z}$ are graphically represented using polar coordinates, and the said impedance $\hat{Z}$ can be represented in both the exponential and the component forms.

The sixth step consists in that the electric coil 2 wound on the arms 1.2 of the ferromagnetic core 1 and connected to the detection and measuring device 18 is set to the frequency $f_{0.5}$ and excited such that the frequency f corresponds to the resonance $$Q_{0.5} = \frac{1}{2} Q_{max};$$

the position of the arms 1.2 of the ferromagnetic core 1 is shifted to the measurement point 22, which is new with respect to the setting according to the first step. The said shifting is performed by the distances dX and dY in the applied system of coordinates 23, where the dX and dY are set to dX=A and dY=B, FIG. 1c. The distances dX and dY are oriented with respect to the surface of the surface of the monitored composite material sample 4, and the air gap 5 is maintained at the defined distance D from the surface of the monitored composite material sample 4. The complex impedance $\hat{Z}$ is recorded in both the component and the exponential forms; after that, there follows a shift by the distances −dX, dY with respect to the original point of measurement I 21, and the complex impedance $\hat{Z}$ is recorded in both the component and the exponential forms. Then a shift by the distances dX, −dY with respect to the initial position of the original point of measurement 21 is performed, and the complex impedance $\hat{Z}$ is recorded in both the component and the exponential forms. Subsequently, a shift by the distances −dX, −dY with respect to the initial position of the original point of measurement 21 is carried out, and the complex impedance $\hat{Z}$ is recorded in both the component and the exponential forms. Then, using the measurements thus performed, we evaluate more accurately the density and volume V of the monitored component in the tested composite material sample 4, the said material being ferromagnetic or ferromagnetic and electrically conductive formations; after that, the established records of the complex impedance $\hat{Z}$ are used to calculate its mean value.

Figure 1B:
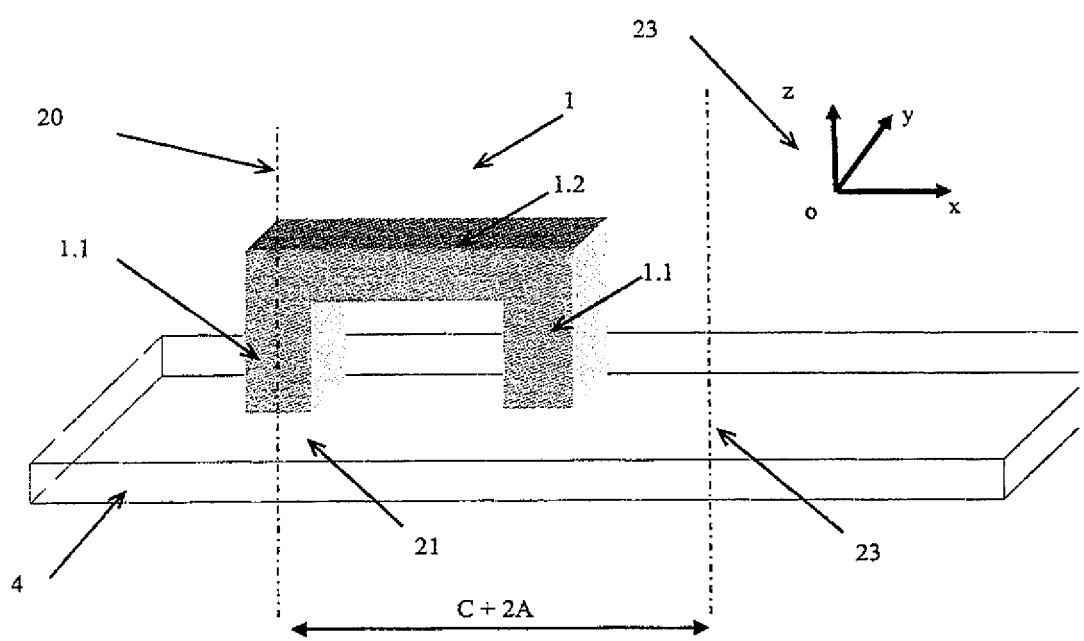
FIG. 1b indicates, according to the described invention, the choice of the ferromagnetic core shift during the actual measurement for the following location of measurement of the complex impedance $\hat{Z}$.
Figure 1C:
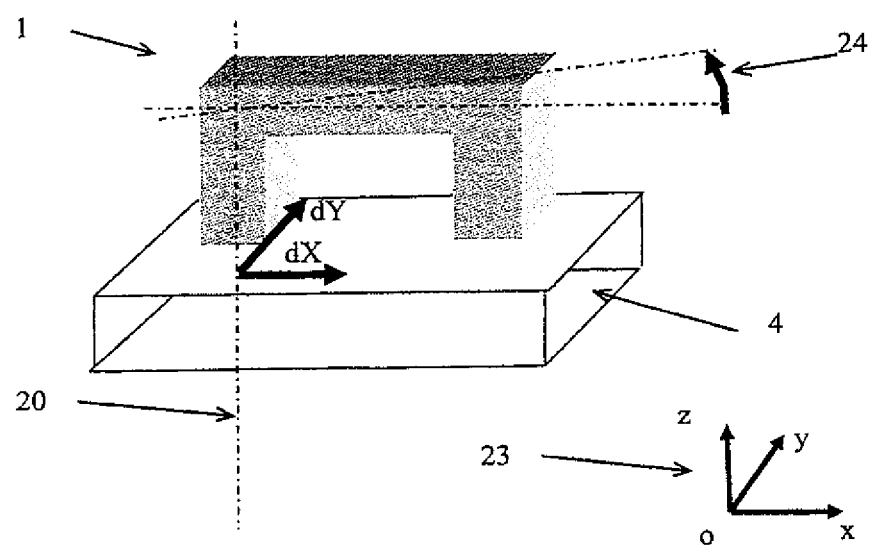
FIG. 1c presents the setting of the shift of the dX and dY of the ferromagnetic core during the measurement.

The seventh step then comprises the positioning of the axis 20 of the ferromagnetic core 1 to a new measurement point 22 of the ferromagnetic core 1; this position is, in the direction of the coordinate x, different by at least a distance greater than the length C of the base 1.1 plus double the width A of an arm 1.2, equalling C+2A, according to the dimensions of the ferromagnetic core 1 (FIG. 1b). After setting the new position of the axis 20 of the ferromagnetic core 1, we measure and evaluate the quantities in accordance with the first to the sixth steps. Thus, we obtain the numerical and graphical evaluation of the distribution, density, and orientation of the monitored component of the tested composite material sample 4, the said material being ferromagnetic or ferromagnetic and electrically conductive formations along the entire surface of the sample

INDUSTRIAL APPLICABILITY

The method described herein is suitable for civil engineering, aviation, and material engineering, where it can be employed as a non-destructive diagnostic technique to examine composite materials with both ferromagnetic fillers and electrically conductive, non-ferromagnetic or ferromagnetic fillers.

SUMMARY OF APPLIED REFERENCE SYMBOLS

1 Feromagnetic core
1.1 Base
1.2 Arm
2 Electric coil
3 Winding terminals
4 Composite material sample
5 Air gap
6 Magnetic circuit/flux Φ
7 Upper limit of the quality factor
8 Lower limit of the quality factor
9 Resonance curve of the quality factor behaviour
10 Elektromagnetic coupling
11 Instantaneous value of the electric voltage
12 Instantaneous value of the electric current
15 Mutual inductance M
16 Electric voltage generator
17 External electric circuit
18 Detection and measuring device,
19 Heel of the resonance curve
20 Ferromagnetic core axis
21 Original point of measurement
22 New measurement point
23 System of coordinates
24 Angle of rotation
Capacity $C_s$
Resistor $R_s$
Inductance $L_s$
Inductance $L_0$
Capacity $C_0$
Resistor $R_0$
dX—distance
dY—distance
f—measuring device frequency

The invention claimed is:
1. A method for the evaluation of the distribution, density and orientation of ferromagnetic, electrically conductive fibres/formations in a composite material, characterised in that, within the first step, electric coils (2) configured on the arms (1.2) of a C, U or E-shaped ferromagnetic core (1) are set to a frequency f and excited at $f_{sq3}$ in such a manner that the frequency f corresponds to resonance with the quality factor of

$$Q_{sq3} = \frac{1}{\sqrt{3}} Q_{max};$$

subsequently, at a position defined by the distance D from the surface of the monitored composite material sample (4), the complex impedance $\hat{Z}$ is recorded in both the component and the exponential forms; Then, within the second step, the position of the ferromagnetic core (1) is changed via rotating it by an angle of rotation (24 along the axis (20) of one of the arms (1.2) of the said core (1), and the complex impedance $\hat{Z}$ in both the component and the exponential forms is measured and recorded; The third step comprises a position change and recording of the complex impedance $\hat{Z}$ according to the second step, and the change of the position of the ferromagnetic core (1) by the angle of rotation (24) is repeated until the arm (1.2) has rotated by 360°; Subsequently, within the fourth step, we use the results from the first to the third steps to evaluate, based on the formulas for the impedance $\hat{Z}$ and the dissipated power P, the mass density of the ferromagnetic or ferromagnetic and electrically conductive formations of the composite material sample (4); the evaluation is performed at the measured location; In the fifth step, the frequency f of the detection and measuring device (18) is set to $f_{0.5}$ in such a manner that the resonance corresponds to the factor $$Q_{0.5} = \frac{1}{2} Q_{max}$$

for the original point of measurement (21) and the distance D, and measurement is performed in accordance with the second and third steps; Then, using the data thus obtained, we evaluate the homogeneity of the distribution and orientation of ferromagnetic or ferromagnetic and electrically conductive formations of the composite material sample (4) at the original point of measurement (21); The sixth step consists in that the electric coil (2) is set to the frequency $f_{0.5}$ and excited in such a manner that the frequency corresponds to resonance with the factor $$Q_{0.5} = \frac{1}{2} Q_{max}$$

and the position of the ferromagnetic core (1) is shifted, by distances dX and dY, to the original point of measurement (21), the said distances dX and dY being oriented with respect to the surface of the monitored composite material sample (4), and the defined distance D from the surface of the monitored composite material sample (4) is maintained; subsequently, the complex impedance $\hat{Z}$ is recorded in both the component and the exponential forms; Then, a shift by the distances −dX, dY with respect to the original point of measurement (21) is performed, and the complex impedance $\hat{Z}$ is recorded in both the component and the exponential forms; after that, there follows a shift by the distances dX, −dY with respect to the original point of measurement (21), and the complex impedance $\hat{Z}$ is recorded in both the component and the exponential forms; finally, a shift by the distances −dX, −dY with respect to the original point of measurement is performed, and the complex impedance $\hat{Z}$ is recorded in both the component and the exponential forms. Then, using the measurements thus performed, we carry out a more accurate evaluation of the density and volume of the monitored component in the tested composite material sample (4), and the established records of the complex impedance $\hat{Z}$ are used to calculate the mean value of the density and volume of the monitored component; The seventh step then comprises the setting of the new position of the ferromagnetic core (1) to the new measurement point (22), which ought to be, in the direction of the coordinate x, different by at least a distance greater than the length C of the base (1.1) plus double the width A of an arm (1.2), equaling C+2A, according to the dimensions of the ferromagnetic core (1); after the setting of the said new position of the ferromagnetic core (1), the quantities are measured and evaluated in accordance with the first to the sixth steps, and we thus obtain the numerical and graphical evaluation of the distribution, density and orientation of the monitored component of the tested composite material sample (4) along its entire surface, the said material being ferromagnetic or ferromagnetic and electrically conductive formations.

2. A device to perform the method of claim 1, comprising a C, U or E-shaped ferromagnetic core (1) with distributed or uniform winding of the electric coil (2) according to the above claim 1, the said device being characterised in that the ferromagnetic core (1) exhibits dimensions A, B, and C, for which we have C≥3 B and B≅A, where A denotes the width of an arm (1.2), B represents the depth of an arm (1.2), and C is the length of the base (1.1) Furthermore, the said ferromagnetic core (1) is equipped with at least two electric coils (2); to ensure strong electromagnetic coupling on the ferromagnetic core (1), the winding of the electric coil (2) is configured on both arms of the ferromagnetic core (1), and the leads of the electric coil (2) winding are, at the winding terminals (3), connected to an external electric circuit (17); in the said circuit, an electric voltage generator (16) with adjustable frequency f and a detection and measuring device (18) are included.

3. The device of claim 2, characterised in that the ferromagnetic core (1) is manufactured of a ferrite material.

4. The device of claim 2, characterised in that the ferromagnetic core (1) is manufactured of a ferrite material coated with an Ni nanolayer.

5. The device of claim 2, characterised in that a detection and measuring device (18) is used to constitute an impedance meter.

* * * * *